United States Patent [19]
Plötz et al.

[11] Patent Number: 5,194,224
[45] Date of Patent: Mar. 16, 1993

[54] MOISTURE INDICATOR FOR A RESPIRATORY PROTECTION DEVICE

[75] Inventors: Claus-Bernd Plötz, Stockelsdorf; Horst Wezurek, Ratzeurg; Gunther Kolbe, Mölln, all of Fed. Rep. of Germany

[73] Assignee: Dragerwerk Aktiengesellschaft, Lubeck, Fed. Rep. of Germany

[21] Appl. No.: 776,823

[22] Filed: Oct. 10, 1991

[30] Foreign Application Priority Data

Nov. 8, 1990 [DE] Fed. Rep. of Germany ....... 4035493

[51] Int. Cl.$^5$ .......................... A62B 7/08; G01N 21/75
[52] U.S. Cl. ......................................... 422/55; 422/88; 422/120; 422/122; 116/2; 128/202.22; 128/202.26; 128/205.28
[58] Field of Search ................... 422/55, 58, 120, 122, 422/83, 88; 436/39–41, 167; 116/2; 252/408; 128/202.22, 202.26, 205.28

[56] References Cited

U.S. PATENT DOCUMENTS

4,019,509  4/1979  Li et al. ............................... 128/147

FOREIGN PATENT DOCUMENTS

2119659  11/1983  United Kingdom .

OTHER PUBLICATIONS

Shereshovets, V. V. et al. "Chemiluminescence in the reaction of alkali metals ozonides with water", Izv. Akad. Nauk SSSR, Ser. Khim., (12), p. 2879, 1988.
Firsova, T. P. et al. "Reaction between potassium ozonide, water vapor, and carbon dioxide", Izv. Akad. Nauk SSSR, Ser. Khim; (5), pp. 973–976, 1967.

Primary Examiner—James C. Housel
Assistant Examiner—David Redding
Attorney, Agent, or Firm—McGlew and Tuttle

[57] ABSTRACT

A moisture indicator for indicating the state of moisture loading of an oxygen-releasing chemical in a respiratory protection device which contains the peroxide of an alkali metal as the substance is to be improved such that it will indicate an irreversible and clearly recognizable color change and will respond to the intrusion of even small amounts of moisture. To accomplish this task, the substance contains as the reactive substance an additive in the form of an alkali metal ozonide that engages in a color reaction with moisture present in the air.

15 Claims, No Drawings

MOISTURE INDICATOR FOR A RESPIRATORY PROTECTION DEVICE

FIELD OF THE INVENTION

The present invention pertains to a moisture indicator for indicating the state of moisture loading of a chemical that releases oxygen in a respiratory protection device that contains the peroxide of an alkali metal.

BACKGROUND OF THE INVENTION

Moisture indicators for oxygen-releasing chemical cartridges are preferably used in respiratory protection devices which protect the users of the protection devices as short-term escape or first-aid devices in atmospheres that are unsuitable for breathing. Such devices are packed hermetically together with the chemical cartridge in a carrying container that is opened only shortly before the use of the device. Since the chemical cartridge reacts to moisture and releases oxygen in this reaction, loading of the chemical cartridge with moisture prior to the use of the device must be avoided. To ensure this, a moisture indicator which monitors the atmosphere surrounding the chemical cartridge inside the device and indicates the breakthrough of moisture via a color change is attached to the carrying container. A chemical cartridge previously damaged by moisture can thus be recognized in time and replaced before the use of the device.

A respiratory protection device with a moisture indicator has become known from German Patent Specification No. DE-PS 33,15,070. The respiratory protection device consists of a carrying container with a chemical cartridge based on potassium peroxide, through which the user of the device breathes by pendular breathing. The carbon dioxide exhaled and the moisture present in the breathing air are bound by the chemical cartridge, and oxygen is released during this reaction. Due to the limited amount of oxygen that can be generated from the potassium peroxide cartridge carried by the user, it is important, before the device is used, to hermetically seal the inside of the carrying container against the intrusion of moisture. This is achieved with a circumferential seal along the seam of the carrying container. Furthermore, a moisture indicator, which detects moisture that has penetrated, is provided. Potassium peroxide, whose color changes irreversibly from yellow to colorless on penetration of moisture, is used as the moisture indicator. Damaged chemical cartridges can thus be recognized and replaced in time, so that the user of the device will always carry with him a respiratory protection device with full protective capacity.

It is disadvantageous in the case of the prior-art moisture indicator that the color change is difficult to recognize if the device is used under unfavorable conditions, e.g., underground. In addition, the moisture indicator is insensitive to the intrusion of small amounts of moisture, which may render the chemical cartridge unfit for use especially during prolonged storage. In this case the chemical cartridge is damaged before the color of the moisture indicator changes.

SUMMARY AND OBJECTS OF THE INVENTION

It is the object of the present invention is to provide an irreversible moisture indicator based on an alkali metal peroxide, which shows a clearly recognizable color change and also responds to the intrusion of small amounts of moisture.

This task is accomplished by a substance containing as the reactive substance an additive in the form of an alkali metal ozonide which engages in a color reaction with moisture present in the air.

The advantage of the present invention is essentially that the addition of an alkali metal ozonide to the alkali metal peroxide leads to the formation of a moisture indicator which leads to improved recognizability of the color change, namely, from brown conditions. In addition, this moisture indicator has a higher sensitivity than a moisture indicator based exclusively on an alkali metal peroxide. The moisture indicator according to the present invention is produced by treating the amount of alkali metal powder needed for the moisture indicator—ca. 2 g—with an oxygen-ozone gas mixture in the absence of moisture until a homogeneous color change from yellow to brown takes place on the surface of the powder grains. The reaction now taking place can be described, e.g., for potassium, by the reaction $$KO_2 + O_3 \rightarrow KO_3 + O_2.$$

A tablet is prepared from the alkali metal powder thus treated with the gas, and this tablet will be used as the moisture indicator. During the subsequent reaction of the moisture indicator with water, $$KO_3 + H_2O \rightarrow KO_2 + H_2O_2$$

is formed from the potassium ozonide in a first intermediate reaction, and the $H_2O_2$ is converted into $$H_2O_2 \rightarrow H_2O + \tfrac{1}{2}O_2$$

in a second intermediate reaction. The yellow color of the peroxide becomes visible.

The reaction of the peroxide with water leads to $$2KO_2 + H_2O \rightarrow 2\,KOH + 1.5O_2,$$

the colorless potassium hydroxide, while oxygen is split off. The higher sensitivity of the moisture indicator according to the present invention can be attributed to the fact that part of the water formed in the second reaction step immediately reacts with the alkali metal ozonide.

Experiments carried out with the moisture indicator according to the present invention have shown that approximately half of the total surface area of the moisture indicator changed color from brown to yellow after about 19 hours of storage of the tablet at room temperature in an indicator housing with simultaneous defined diffusion of ambient moisture into the interior of the housing. The color change from yellow to colorless during the experiment occurred in an area corresponding to only 10% of the total surface area in the area of diffusion. Consequently, only 10% of the total surface would show a color change in the case of a prior-art moisture indicator based exclusively on alkali metal, whereas the moisture indicator according to the present invention already indicates a color change covering half of the total surface area. In this case, the diffusion of the ambient air into the moisture indicator took place via a cross sectional area corresponding to 7 holes with a hole diameter of 0.6 mm. The temperature stability of the moisture indicator is sufficient for use in respiratory protection devices.

Advantageous embodiments of the present invention are disclosed. The alkali metals potassium, rubidium, and cesium can be used as the substances for the moisture indicator. Treatment with the oxygen-ozone gas mixture leads to a color change from yellow to brown in all cases. The color change taking place under the effect of water is from brown to colorless via yellow in the case of the above-mentioned alkali metals.

It is advantageous to use the moisture indicator in the form of a tablet introduced into an indicator housing which is provided with a viewing window and diffusion openings through which the atmosphere surrounding the chemical cartridge is able to penetrate into the interior of the housing. The color change from brown to colorless via yellow begins at the diffusion openings and proceeds from here to cover the entire indicator surface.

DETAILED DESCRIPTION OF THE INVENTION

The present invention will be explained on the basis of two examples.

1. Potassium peroxide or cesium peroxide powder is treated with a gaseous mixture of oxygen and ozone with an ozone content of 4% in a fluidized bed reactor in the absence of moisture at a temperature of 0°-15° C. A change in the color of the powder from yellow to brown takes place within a gas treatment time of ca. 3 minutes. The powder is subsequently pressed into tablets under a dry atmosphere. The tablets have a diameter of 19 mm and a thickness of 4.5 mm. As an alternative to peroxide powder, it is also possible to subject granular product or tablets to the gas treatment. The tablets are introduced as a moisture indicator into the indicator housing.

2. A tablet consisting of rubidium peroxide with a diameter of 19 mm and a thickness of 4.5 mm is treated with a gaseous reaction vessel in the absence of moisture at a temperature of 0°-20° C. The color of the tablet changes from yellow to brown within a gas treatment time of ca. 3 minutes. Under the effect of water, the color changes back from brown to colorless via yellow. As an alternative to rubidium peroxide tablets, it is also possible to subject rubidium peroxide powder or granules to the gas treatment and to subsequently press them into tablets.

While specific embodiments of the invention have been shown and described in detail to illustrate the application of the principles of the invention, it will be understood that the invention may be embodied otherwise without departing from such principles.

What is claimed is:

1. A moisture indicator for indicating a degree of moisture loading of an oxygen-releasing chemical in a respiratory protective device comprising peroxide of an alkali metal as the oxygen-releasing chemical, wherein the improvement comprises:
a reactive substance in the form of an alkali metal ozonide providing a color reaction with moisture present in air.

2. A moisture indicator according to claim 1, wherein said reactive substance is potassium ozonide and said alkali metal peroxide is potassium peroxide.

3. A moisture indicator according to claim 1, wherein said reactive substance is rubidium ozonide and said alkali metal peroxide is rubidium peroxide.

4. A moisture indicator according to claim 1, wherein said reactive substance is cesium ozonide and said alkali metal peroxide is cesium peroxide.

5. A moisture indicator according to claim 1, wherein said reactive substance, alkali metal ozonide, is in the form of disk-shaped tablets and accommodated in an indicator housing which further comprises a viewing window and diffusion openings for atmosphere surrounding said chemical.

6. A moisture indicator according to claim 2, wherein said reactive substance, alkali metal ozonide, is in the form of disk-shaped tablets and accommodated in an indicator housing which further comprises a viewing window and diffusion openings for atmosphere surrounding said chemical.

7. A moisture indicator according to claim 3, wherein said reactive substance, alkali metal ozonide, is in the form of disk-shaped tablets and accommodated in an indicator housing which further comprises a viewing window and diffusion openings for atmosphere surrounding said chemical.

8. A moisture indicator according to claim 4, wherein said reactive substance, alkali metal ozonide, is in the form of disk-shaped tablets and accommodated in an indicator housing which further comprises a viewing window and diffusion openings for atmosphere surrounding said chemical.

9. A respiratory protective device comprising:
a cartridge through which a user breathes containing an oxygen-producing means;
an alkali metal ozonide located in said cartridge, said alkali metal ozonide reacting with moisture to cause a change in color of said alkali metal ozonide;
viewing window means for observing said color of said alkali metal ozonide, said viewing window means being on said cartridge.

10. A device in accordance with claim 9, wherein:
said change in color is in a visible spectrum.

11. A device in accordance with claim 9, wherein:
said change in color is detected by a change in reflective light.

12. A device in accordance with claim 9, wherein:
said change in color is from brown to yellow.

13. A device in accordance with claim 9, wherein:
said alkali metal ozonide reacts with moisture to provide an alkali metal peroxide which further reacts with moisture to produce oxygen.

14. A device in accordance with claim 9,
wherein said oxygen producing means is an alkali metal peroxide located in said cartridge and reacting with moisture to provide oxygen for respiration of the user.

15. A moisture detector indicating a presence of water by a change of visible reflective light, the detector comprising:
a cartridge means containing alkali metal ozonide.

* * * * *